United States Patent [19]

van Andel

[11] Patent Number: Plant 5,500

[45] Date of Patent: Jun. 25, 1985

[54] CARNATION NAMED MUREDO

[75] Inventor: Jacob van Andel, Aalsmeer, Netherlands

[73] Assignees: B. V. Handelskwekerij; M. C. van Staaveren, both of Aalsmeer, Netherlands

[21] Appl. No.: 556,456

[22] Filed: Nov. 30, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new variety of miniature carnation of the spray type particularly distinguished by its profuse production of flowers and particularly more flowers per stem than normally occurs on plants of the miniature carnation type, and by its strong, upright growth habit and rapid production of blooms.

1 Drawing Figure

BACKGROUND OF THE NEW PLANT

This new variety of miniature carnation originated as a seedling hybrid of two unnamed and unpatented varieties growing among my collection of miniature carnation plants maintained at Aalsmeer, The Netherlands, for breeding purposes, this particular plant being selected by me for propagation and test because of its relative large production of blooms with many more per stem than ordinarily occurs in carnation plants of this type. The flower color was also a determining factor with respect to the selection of this plant and the plant was propagated by means of cuttings with such favorable results with respect to growth habit and rate of flower production that I continued such production through several successive generations at Aalsmeer and thereby determined that the distinctive and advantageous characteristics of this plant would hold true from generation to generation and appeared to be firmly fixed.

DESCRIPTION OF THE DRAWING

My new variety of carnation plant is illustrated by the accompanying drawing which shows a group of flower stems with buds and opening flowers in various stages to full bloom, the drawing being a full color photographic rendition with the colors shown being as nearly true as it is reasonably possible to obtain by conventional photographic procedures.

DESCRIPTION OF THE NEW PLANT

The following is a detailed description of my new variety of miniature carnation as observed of greenhouse plants in the early summer of 1983, the color designations being according to The R.H.S. Colour Chart published by The Royal Horticultural Society of London, England.

THE PLANT

Origin: Seedling.

Parentage: Both seed parent and pollen parent being unknown and unpatented varieties.

Classification:

Botanic.—Hybrid *Dianthus caryophyllus.*

*Commercial.*—Miniature carnation.

Form: Tall bush of the spray type.

Height: Various depending on season.

Growth: Strong and upright with normal branching character.

Foliage:

*Quantity.*—Moderate.

*Size of leaf.*—Medium and of lanceolate shape.

*Texture.*—Smooth.

*Color.*—Upper side — Grey/Green. Under side — Grey/Green.

Petioles: None. The leaf is sessile.

THE BUD

Form: Ovoid body with pointed apex becoming cylindrical as sepals begin to divide and flower appears.

Size: Small.

*Diameter.*—About 10 mm.

*Length.*—About 20 mm.

Opening rate: Moderate.

Sepals:

*Shape.*—Generally oblong with acute apex. The sepals stand up when flowers open.

*Color.*—Inside — Grey/Green. Outside — Grey/-Green.

Calyx:

*Shape.*—Funnel-shaped.

*Size.*—Medium and long.

*Aspect.*—Smooth.

*Splitting.*—The calyx rarely splits.

Flower stem:

*Length.*—Long and depending on season.

*Character.*—Rigid and erect.

*Color.*—Grey/Green.

THE FLOWER

Blooming habit: Profuse and continuous.

Size of bloom: Small.

*Diameter.*—40 mm.

*Depth.*—20 mm.

Borne: Singly.

Shape: High centered.

Petalage:

*Number of petals.*—About 30 to 40.

*Form.*—Fan-shaped with serrate margin.

*Texture.*—Soft.

*Appearance.*—Shiny.

*Color.*—Outer and inside petals: Top side: Body — R.H.S. 46C. Base — Pale Green. Reverse side — R.H.S. 46C. Color is the same for all seasons.

Flower stem:

*Length.*—Depending on season.

*Character.*—Strong and upright.

*Color.*—Grey/Green.

Persistence: The petals hang on and dry.

Fragrance: Weak.

Disease resistance: This flower is less susceptible to fusarium oxysporum as observed in the Aalsmeer district of The Netherlands.

Lasting quality:

*On plant.*—Approximately 15 days.

*As cut flower.*—About 10 days.

REPRODUCTIVE ORGANS

Stamens:

*Number.*—Medium.

*Anthers.*—Size: Medium. Color: Cream.

*Filaments.*—Color: White with pink top.

Pistils:

*Number.*—One.

*Style.*—Length: Approximately 30 mm. Color: Red.

*Stigma.*—Color: Red.

The advantageous characteristics of this new miniature carnation reside in its rapid and excellent production of blooms, a larger number of small flowers per flower stem, and its being less susceptible to fusarium oxysporum.

I claim:

1. The new and distinct variety of miniature carnation, substantially as herein shown and described, characterized in particular by rapid production of blooms and a larger number of blooms per flower stem.

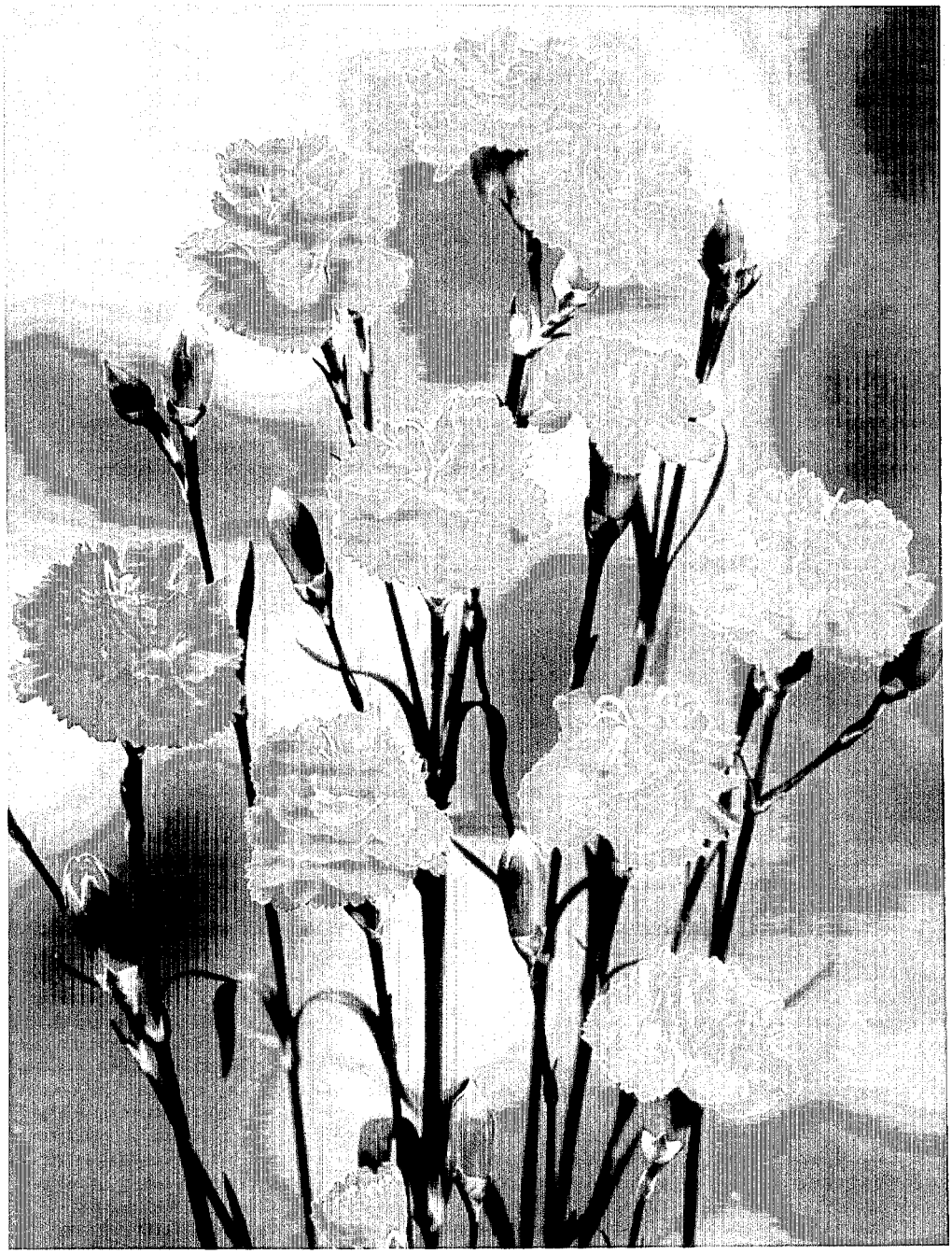

* * * * *